United States Patent
Warner et al.

(10) Patent No.: US 9,591,980 B2
(45) Date of Patent: Mar. 14, 2017

(54) MULTI-DEVICE CONNECTOR FOR PATIENT INTERFACE

(71) Applicant: General Electric Company, Schenectady, NY (US)

(72) Inventors: Adrian F. Warner, Wauwatosa, WI (US); Daniel Joseph Nowicki, Wauwatosa, WI (US); Daniel Richard Schneidewend, Wauwatosa, WI (US); Rodger F. Schmit, Wauwatosa, WI (US); Timothy P. Stiemke, Wauwatosa, WI (US)

(73) Assignee: General Electric Company, Schenectady, NY (US)

( * ) Notice: Subject to any disclaimer, the term of this patent is extended or adjusted under 35 U.S.C. 154(b) by 2 days.

(21) Appl. No.: 14/586,232

(22) Filed: Dec. 30, 2014

(65) Prior Publication Data

US 2016/0183825 A1    Jun. 30, 2016

(51) Int. Cl.
   *A61B 5/04*      (2006.01)
   *A61B 5/0408*    (2006.01)
   *A61B 5/0215*    (2006.01)

(52) U.S. Cl.
   CPC ........ *A61B 5/0408* (2013.01); *A61B 5/02158* (2013.01); *A61B 2562/226* (2013.01); *A61B 2562/227* (2013.01)

(58) Field of Classification Search
   CPC .. A61B 5/0408; A61B 5/02158; H01R 13/665

USPC ........................................................ 600/509
   See application file for complete search history.

(56) References Cited

U.S. PATENT DOCUMENTS

| 5,813,991 A | 9/1998 | Willis et al. |
| 2009/0177046 A1* | 7/2009 | Zhang ................. A61B 5/0002 600/300 |

OTHER PUBLICATIONS

"ECG Out Cable—Application Note", Philips Healthcare, 3000 Minuteman Road, Andover, MA 01810-1085, Published Aug. 2011, Edition 2, 4 pages.

* cited by examiner

*Primary Examiner* — Paula J Stice
(74) *Attorney, Agent, or Firm* — Boyle Fredrickson, S.C.

(57) ABSTRACT

A multi-device connector for ECG signals permits multiple medical devices to share patient-connected surface electrodes, providing a patient-side terminal set having a direct connection to one device-side terminal set and buffered connections to multiple additional device-side terminal sets. Invasive blood-pressure sensor readings may also be shared by providing a direct connection between a patient-side terminal set and multiple device-side terminal sets for blood-pressure signals and a direct connection between the patient-side terminal set and only one device-side terminal set. Indirect, scaled connections between the remaining device-side terminal sets and the patient-side terminal set may be provided.

12 Claims, 5 Drawing Sheets

MULTI-DEVICE CONNECTOR FOR PATIENT INTERFACE

STATEMENT REGARDING FEDERALLY SPONSORED RESEARCH OR DEVELOPMENT

--

CROSS REFERENCE TO RELATED APPLICATION

--

BACKGROUND OF THE INVENTION

The present invention relates to electronic equipment for patient monitoring, recording, or triggering type applications, in particular to an interface that allows sharing of ECG and/or blood-pressure signals among multiple medical devices.

During treatment of a patient, the patient may be monitored through surface electrodes attached to the patient's skin, or other sensors, such as blood-pressure sensors, contained within a catheter inserted into the patient. Frequently, multiple different medical devices will require signals from the same electrodes or sensors. For example, ECG signals from skin electrodes may be required by a patient monitoring device for displaying ECG signals, a recording device recording those signals, a mapping device locating intracardiac electrodes, and a respiration sensor using the electrodes (but not the signals) for respiration monitoring. Similarly, blood-pressure information from a single blood-pressure sensor may be required by different medical devices.

Ideally multiple devices could share electrodes or other sensors such as catheter blood-pressure sensors to avoid exceeding the limited number of connections that can be practically made between devices and the patient. In practice, this sharing can be difficult. Attaching multiple devices to a given electrode may unduly load the electrode, reducing the signal and increasing noise. Often, some uses of a given set of electrodes will be incompatible with other uses. For example, when an ECG monitoring system injects current into the ECG signal for impedance measurement, the injected signals may conflict or interfere with measurements made by other connected medical devices. With respect to blood-pressure sensors, it is not uncommon for different monitoring devices to apply different excitation voltages to the blood-pressure sensors and to expect blood-pressure signals in different voltage ranges.

SUMMARY OF THE INVENTION

The present invention provides a connector that can connect multiple medical devices to a limited number of patient connections for ECG signals and/or blood-pressure signals. The possibility of incompatible ECG electrode usage among the different medical devices is addressed by flexibly allowing one connected device to maintain a direct electrical connection with the patient while buffering the remaining electrical devices with one-way connections. A pressure sensor may be shared by monitoring the excitation signals from the various devices, blocking all but one, and scaling a return signal according to the permitted excitation signal and the monitoring of the other excitation signals.

Specifically, the present invention provides a multi-device connector for interfacing patient signals and having a first set of terminals receiving patient electrical conductors from patient-connected surface electrodes and at least a second, third and fourth set of terminals receiving electrical conductors from medical devices requiring electrical communication with the patient electrical leads. A bidirectional electrical conductor provides a bidirectional electrical connection between the first set of terminals and only a given one of the second, third and fourth set of terminals. Buffer amplifiers provide independent connection between each of the first set of terminals and each of the of the second, third and fourth set of terminals other than the given one of the second, third and fourth set of terminals.

It is thus a feature of at least one embodiment of the invention to provide a simple and intuitive method of sharing limited patient connections with multiple electrical devices while managing incompatible uses.

The buffer amplifiers may be high impedance unity gain amplifiers having an input impedance of over one megaohm.

It is thus a feature of at least one embodiment of the invention to prevent detrimental loading of low-power signals, for example, ECG signals when they are shared by multiple devices.

The first, second, third, and fourth set of terminals may each provide ten terminals for receiving ten patient conductors associated with a 12-lead ECG acquisition.

It is thus a feature of at least one embodiment of the invention to provide a system that allows sharing of standard 12-lead ECG surface electrodes.

The multi-device connector may further include at least one fifth set of electrical terminals and may include differential amplifiers having inputs receiving different signals from different patient-connected surface electrodes through the first set of terminals and providing lead outputs being the difference of those inputs.

It is thus a feature of at least one embodiment of the invention to permit the connector to work with mixed devices, some requiring 12-lead ECG signals and some requiring single-lead ECG signals.

The multi-device connector may further include a switch matrix positioned between the first set of terminals and the second, third, and fourth set of terminals operating to change the given one of the second, third, and fourth set of terminals.

It is thus a feature of at least one embodiment of the invention to permit rapid changing of a "master" device having bidirectional access to the patient without rewiring the devices to the multi-device connector.

The multi-device connector may further include a visual indicator indicating which of the second, third, and fourth set of terminals is the given one of the second, third, and fourth set of terminals.

It is thus a feature of at least one embodiment of the invention to provide a clear indication to the user of the routing of multiple signals in the multi-device connector.

The multi-device may further include a sixth set of terminals receiving patient electrical conductors from a patient-connected to an invasive blood-pressure sensor and at least a seventh, eighth and ninth set of terminals receiving device electrical conductors from medical devices requiring electrical communication with the invasive blood-pressure sensor of a type receiving an excitation signal to provide a blood-pressure signal. Each of the sixth, seventh, eighth and ninth set of terminals may provide separate terminals for excitation signals and blood-pressure signals. The multi-device connector may further include blood-pressure signal conductors providing a connection between the terminals for blood-pressure signals of the sixth set of terminals and the seventh set of terminals, and excitation signal conductors providing a connection between the terminals for excitation signals of the sixth set of terminals and the seventh set of terminals for communication of excitation signals between the seventh set of terminals and sixth set of terminals. Measurements circuits connected to the terminals for excitation signals of the seventh, eighth and ninth set terminals may produce measurement signals measuring the excitation signals from the connected medical devices, and amplitude adjustment circuits may receive the blood-pressure signals from the sixth set of terminals and provide them independently to the eighth and ninth sets of terminals after amplitude adjustment according to a ratio of two measurement signals, the first measurement signal measuring the excitation signal from the seventh set of terminals and the second measurement signal measuring the excitation signal from a respective one of the eighth and ninth set of terminals receiving an output from a given adjustment circuit for blood-pressure signals for a respective one of the eighth and ninth set of terminals.

It is thus a feature of at least one embodiment of the invention to allow the connection of multiple different devices to a single bridge-type pressure sensor even when the different multiple devices provide different excitation voltages and expect pressure signals in different ranges.

The measurement circuits may be differencing amplifiers and the amplitude adjustment circuit may be a variable gain amplifier accepting ratio metric inputs.

It is thus a feature of at least one embodiment of the invention to provide a simple embodiment in which the signal adjustments are accomplished with discrete analog circuits.

Alternatively, the measurement circuits may be analog-to-digital converters and the amplitude adjustment circuit may be a microprocessor communicating with separate digital analog converters for each of the eighth and ninth set of terminals.

It is thus a feature of at least one embodiment of the invention to provide a robust digital implementation of the connector system.

These particular objects and advantages may apply to only some embodiments falling within the claims and thus do not define the scope of the invention.

DETAILED DESCRIPTION OF THE PREFERRED EMBODIMENT

Figure 1:
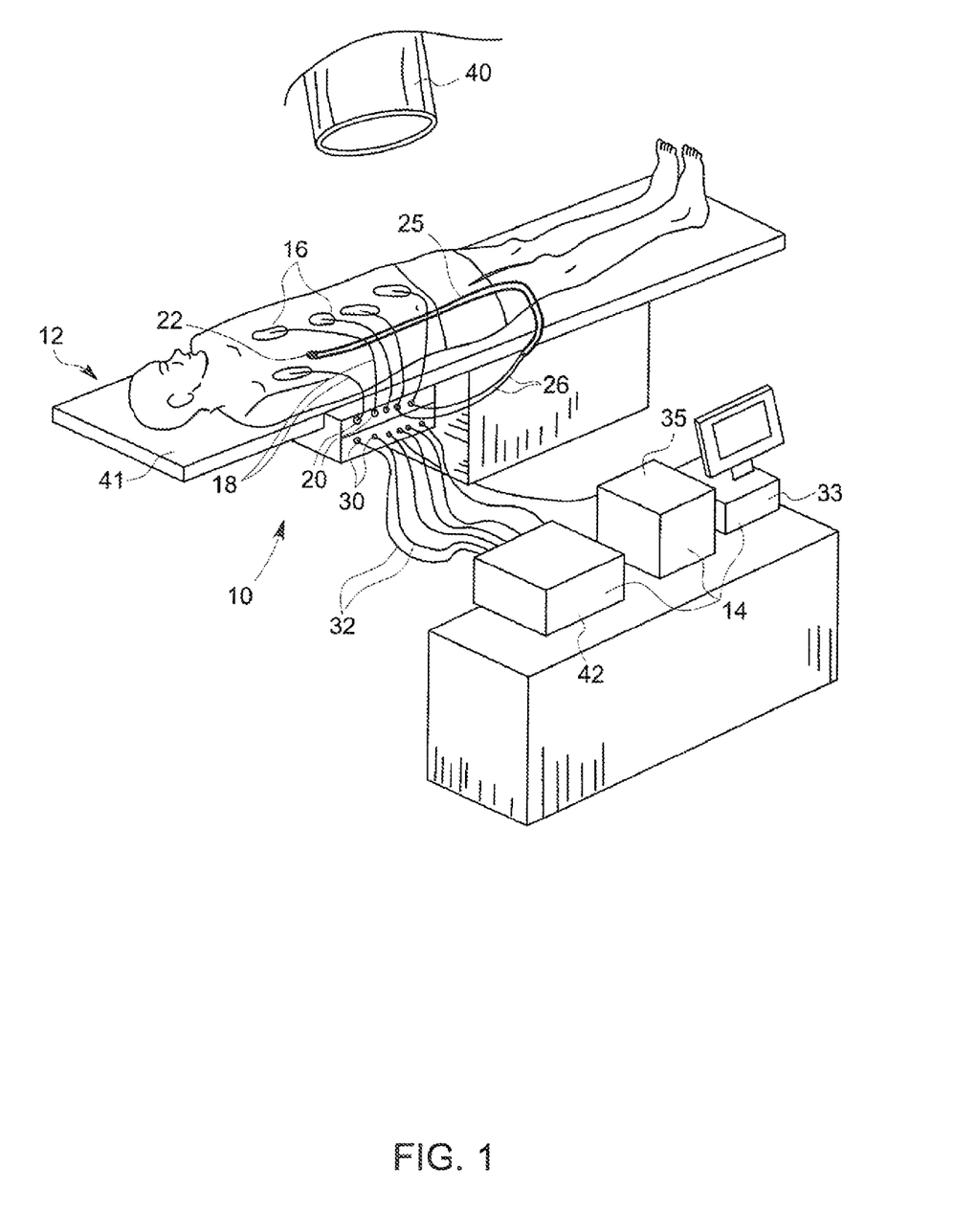
FIG. 1 is a perspective view of a patient table of the type that may incorporate the multi-device connector of the present invention showing the multi-device connector positioned between patient-connected conductors and medical devices requiring access to those conductors.

Referring now to FIG. 1, the multi-device connector 10 of the present invention may provide a gateway between a patient 12 and multiple medical devices 14 including those requiring ECG and/or blood-pressure signals.

In one example, the patient 12 may have multiple surface ECG electrodes 16 communicating via ECG conductors 18 to patient-side terminals 20 on the multi-device connector 10. Intravenous pressure sensor 22, introduced within the patient 12 through a catheter 25 may also communicate with patient-side terminals 20 via pressure sensing conductors 26 attached to patient-side terminals 20 on the multi-device connector 10.

Conversely, the medical devices 14 may connect to the multi-device connector 10 via conductors 32 leading from device-side terminals 30 on the multi-device connector 10 to the medical devices 14.

By way of example, the medical devices 14 may include 12-lead ECG devices 14 and single-lead ECG devices. The 12-lead ECG devices 14 may include a patient monitor 33 providing for visual display and automatic monitoring of the signals from the surface ECG electrodes 16 and/or pressure sensor 22. The 12-lead ECG devices 14 may also include a recorder unit 35 synchronously recording ECG signals from surface ECG electrodes 16 and pressure sensor 22 and/or a mapping unit 42 processing signals from the ECG electrodes 16 to track intra-cardiac electrodes (not shown). An example mapping unit 42 suitable for use with the present invention is manufactured by Biosensor Webster under the trade name Carto3® and employs technology described in U.S. Pat. No. 5,813,991 hereby incorporated by reference.

The medical devices 14 may also include one or more single-lead ECG devices 14 such as a strip recorder, stimulator, fluid pump, and/or a medical imaging device 40 such as an x-ray machine, CT machine, MRI machine or the like, these latter imaging machines using ECG signals to produce gated images, for example, of the heart 24 timed to particular physiological periods such as a heartbeat or respiration cycle.

The multi-device connector 10 may be conveniently mounted on a table 41 supporting the patient 12 or otherwise integrated into the structure of the table 41 to provide a stable connection point between the conductors 26 of the catheter 25 and ECG conductors 18 and the patient-side terminals 20, the latter of which may move with motion of the patient table 41 and patient 12.

Figure 2:
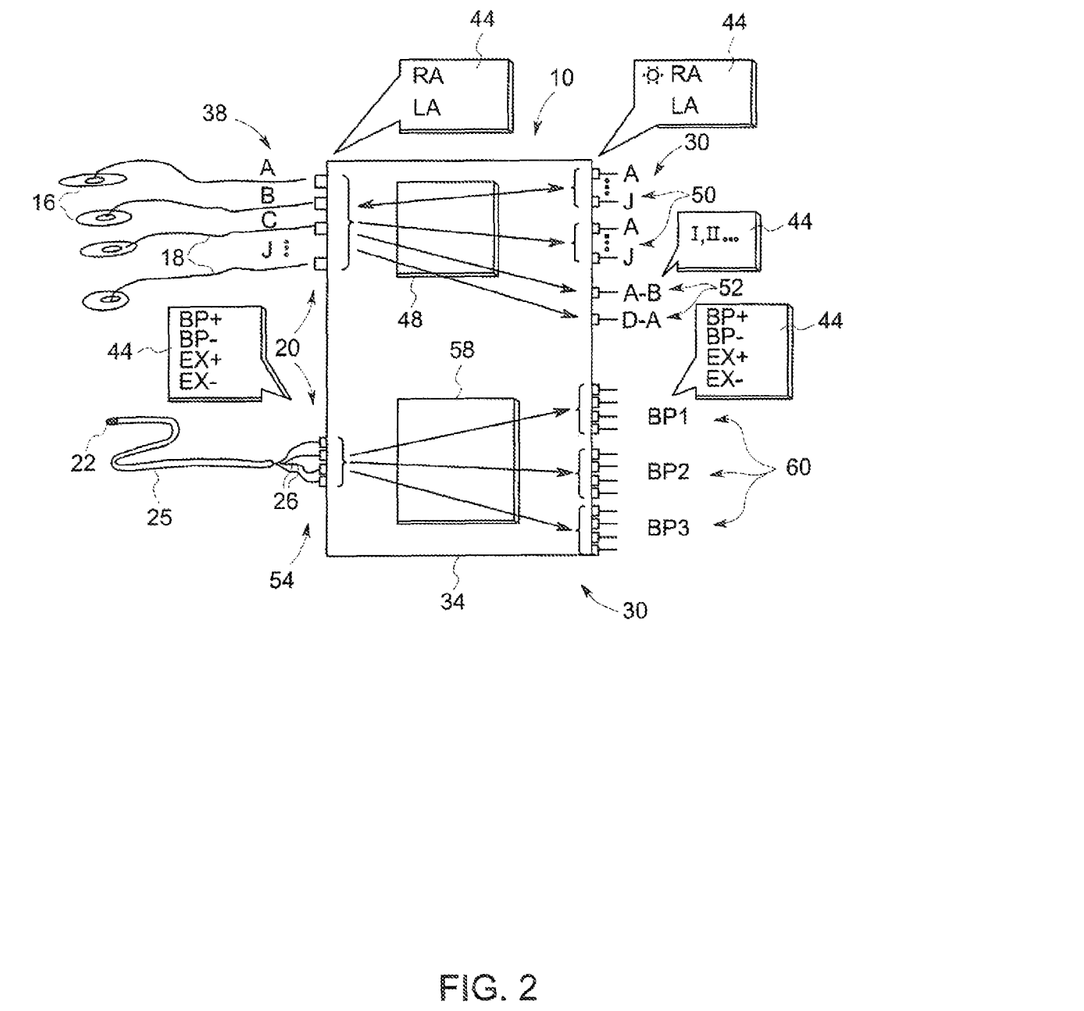
FIG. 2 is a simplified block diagram of one embodiment of the present invention showing the various conductor sets communicating between the patient connections and the medical devices and showing subsystems for ECG and blood-pressure interconnection.

Referring now to FIG. 2, the multi-device connector 10 may provide a housing 34 supporting the patient-side terminals 20 and device-side terminals 30 and, as noted above, attached to the table 41. Each of these patient-side terminals 20 and device-side terminals 30 provide releasable electrical connectors of the type known in the art.

The patient-side terminals 20 may include an ECG terminal set 38 consisting of 10 patient-side terminals 20 designated in FIG. 2 for purposes of explanation as A-J. The patient-side terminals 20 of terminal set 38 will also be labeled with printed labels 44 or the like readable by a user, the labels 44 providing the standard descriptions for 12-lead ECG including: right arm (RA), left arm (RL), right leg (RL), left leg (LL), and V1, V2, V3, V4, V5, V6.

The device-side terminals 30 will communicate signals between the patient-side terminals 20 and multiple ECG terminal sets 50 (typically multi-device connectors) as distributed by ECG distribution circuit 48. Each 12-lead ECG terminal set 50 also provides ten device-side terminals 30 corresponding to patient-side terminals 20 A-J. Each of the device-side terminals 30 of each 12-lead ECG terminal set 50 will also be labeled with labels 44 indicating the standard designations of right arm (RA), left arm (RL), right leg (RL), left leg (LL), and V1, V2, V3, V4, V5, V6.

Signals received on the patient-side terminals 20 of ECG terminal set 38 will also be distributed by the ECG distribution circuit 48 to corresponding device-side terminals 30 of single-lead ECG terminal sets 52 normally connected to the single-lead ECG devices 14 discussed above. The single-lead ECG terminal sets 52 are typically labeled, with labels 44 readable by the user providing Roman numerals such as (I, IL, III . . . ) according to standard single ECG lead designations.

The patient-side terminals 20 may also include a blood-pressure terminal set 54 consisting of four patient-side terminals 20 providing two terminals for conveying a blood pressure signal and labeled as such with labels 44 (e.g. BP+ and BP−) and two terminals for conveying an excitation signal and labeled as such with labels 44 (e.g. EX+, EG−).

Signals received on the patient-side terminals 20 of the blood-pressure terminal set 54 will be distributed by a blood-pressure distribution circuit 58 to corresponding device-side terminals 30 of blood-pressure terminal sets 60 (captioned in FIG. 2 as BP1, BP2, and BP3). Each of the device-side terminals 30 and blood-pressure terminal sets 60 will also be labeled with labels 44 (i.e. BP+, BP−, EX+, and EG−) to distinguish between the blood-pressure signals and the excitation signals so that proper connections may be made with the devices 14.

Figure 3:
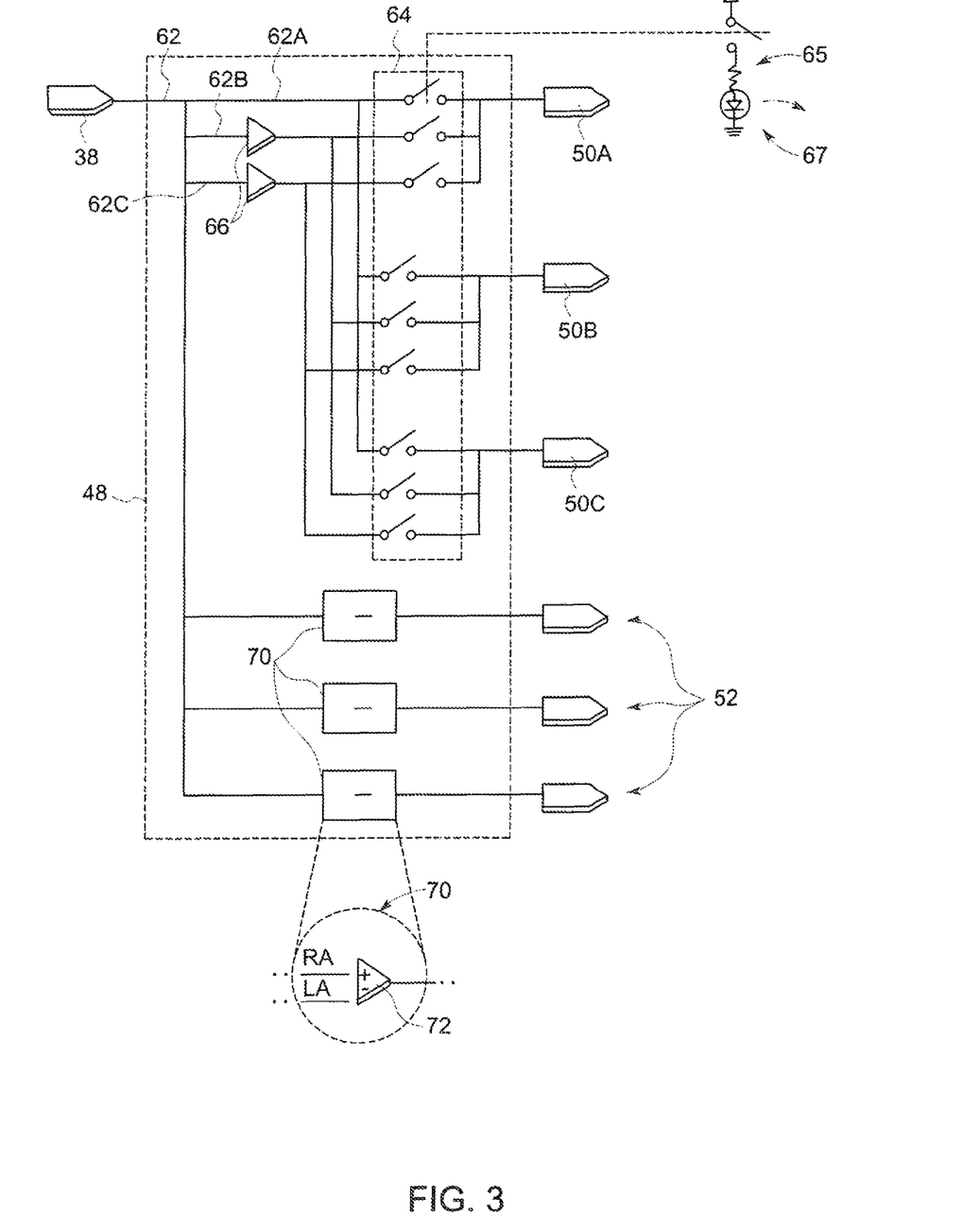
FIG. 3 is a detailed representation of the subsystem for ECG interconnection.

Referring now to FIG. 3 the ECG distribution circuit 48 may include a set of conductors 62 associated with each of the patient-side terminals 20 of the ECG terminal set 38. In this figure the set of conductors 62 is represented as a single line for clarity according to standard schematic conventions. Accordingly, the single line of conductors 62, as represented, should be understood to be multiple independent conductors and provide for multiple independent connections, for example, to independent switches and terminals that will be also represented and described below.

The set of conductors 62 may be separated into three groups 62a-62c, one group 62a communicating directly with switch array 64 and the other two groups 62b-62c communicating through buffer amplifiers 66 (one for each conductor) and then proceeding to the switch array 64. Buffer amplifiers 66 are preferably unity gain operational amplifiers providing a high input impedance, for example, using a field effect transistor input stage and may have input impedance much in excess of one megaohm.

The switch array 64 may be realized either with electromechanical switches (such as reed switches) or solid-state devices and may provide for unidirectional or bidirectional current flow as will be discussed below or evident from context. Generally the switch array 64, for each conductor of the set of conductors 62, will provide a multi-pole, multi-throw switch with the number of poles and the number of throws equal to the number of ECG terminal sets 50. In this example, with three ECG terminal sets 50a-50c, switch array 64 will provide for a three-pole, three-throw switch where the three poles are connected individually to respective conductors of one of groups 62a-62c, and a different one of each of the polls (for each conductor of the set of conductors 62) is connected to a different of the ECG terminal sets 50a-50c. As a result, by operation of the switch array 64, group 62a (providing bidirectional communication between ECG terminal set 38 and one of ECG terminal sets 50) may be switched to any one and only one of the ECG terminal sets 50a-50c. That particular 12-lead ECG terminal set 50 will be associated with what will be termed a "master" medical device 14 and provides for bidirectional current flow between the particular 12-lead ECG terminal set 50 and the ECG terminal set 38. The other two groups 62b and 62c passing through the buffer amplifiers 66 provide unidirectional current flow to the remaining ECG terminal sets 50.

It will be appreciated that by allowing one direct connection to a master medical device (e.g. on ECG terminal sets 50a), that master medical device may not only receive signals from the surface ECG electrodes 16 but may also inject signals from the medical device 14 into those electrodes 16, for example, for impedance measurements which may be used to identify proper connection of the electrodes 16, the particular location on the body of the electrodes 16, or other impedance-based measurements such as respiration. In this way sharing of signals from the electrodes 16 among multiple medical devices 14 may be accomplished while also providing greater functionality for one medical device 14 without conflicts with the other medical devices 14 which may only receive and not inject signals.

Ancillary switch system 65 may provide for an illuminated indicator 67 such as an LED or the like that shows the particular one of ECG terminal sets 50a-50c that is associated with the master medical device.

The set of conductors 62 may also be received by a set of differential amplifiers 70 in the ECG distribution circuit 48 which provides single-lead ECG terminal sets 52. These differential amplifiers 70 may be, for example, high impedance differential amplifiers 72 also having input impedance of excess of one megaohm and optionally a unity gain. Each of the amplifiers 72 may receive as inputs different pairs of the set of conductors 62 and thus are not duplicated for each of the conductors of the set of conductors 62 as is the case with buffer amplifier 66. The particular pairs of the set of conductors 62 are according to standard conventions to provide a single-lead ECG terminal set 52 conforming to standards in this field. For example, in one embodiment, one differential amplifier 72 may provide an output I by subtracting the left arm signal LA from the right arm signal RA as shown in FIG. 3. Other single-lead ECG terminal sets 52 that may be generated include output II being left leg LL minus right arm RA or output 111 being left leg LL minus left arm LA. Each of these single-lead ECG terminal sets 52 may be provided by the ECG distribution circuit 48 to device-side terminals 30 which may be labeled with labels 44 designating I, II III, etc. (as shown in FIG. 2). Clearly the output of the differential amplifiers 70 will only be a single conductor providing the single-lead ECG terminal sets 52. In this way multiple devices requiring a single ECG lead may be accommodated.

Figure 4:
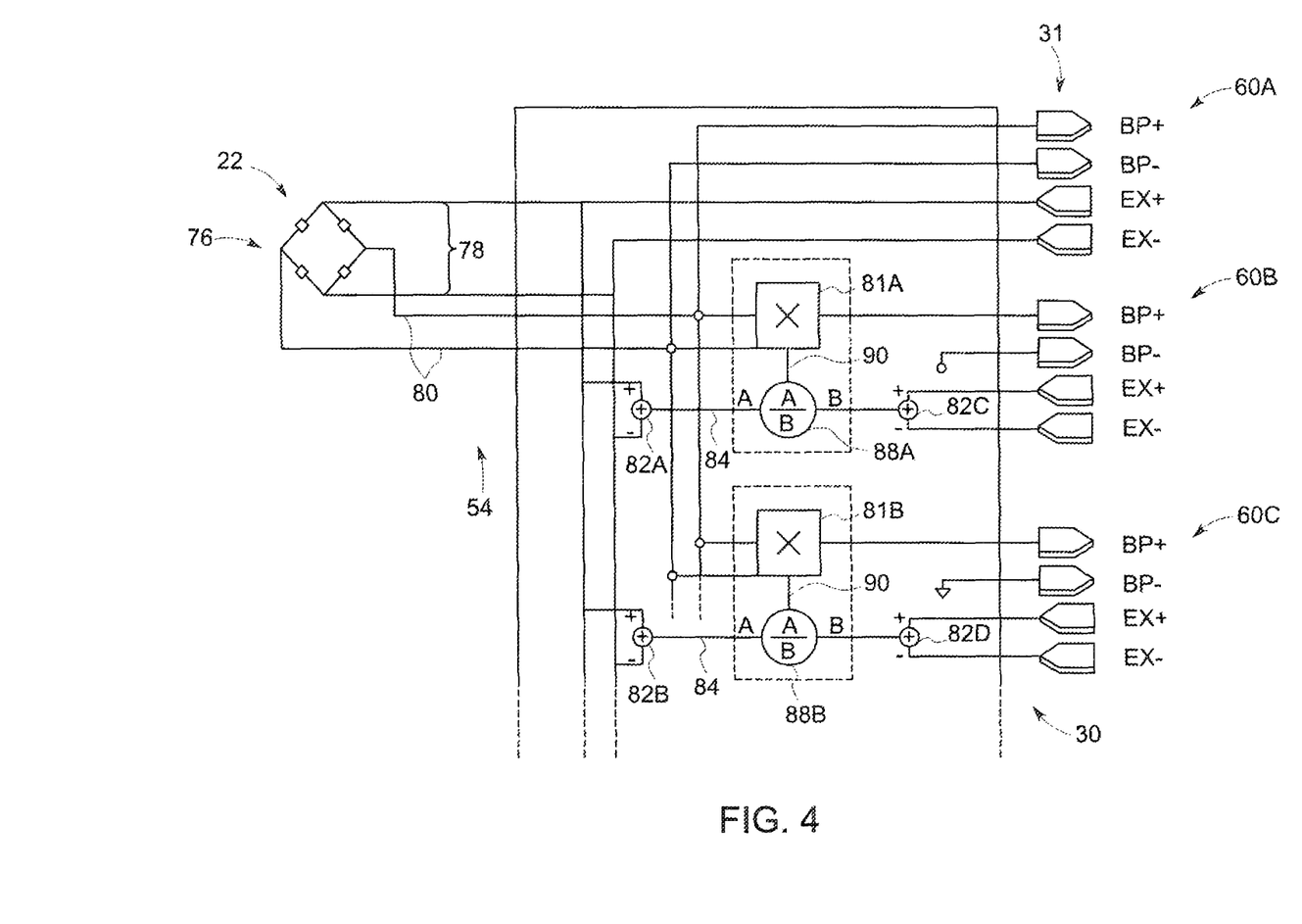
FIG. 4 is a detailed representation of the blood-pressure subsystem showing a block diagram and analog implementation.

Referring now to FIG. 4, the blood-pressure sensor 22, for example, may employ a bridge circuit 76 of the type known in the art requiring application of an excitation signal through conductors 78 and providing a blood-pressure signal through leads 80. As noted, different medical devices 14 may be attached to blood-pressure terminal sets 60 (here designated blood-pressure terminal sets 60a, 60b, and 60c) of the multi-device connector 10. Each of these medical devices 14 may provide a corresponding and possibly different excitation signal to the multi-device connector 10 through corresponding device-side terminals 30. In particular the excitation signals may have different AC voltages. In addition, each of the different medical devices 14 may receive from a corresponding blood-pressure terminal set 60a, 60b, and 60c a blood-pressure signal. Generally the different medical devices 14 will expect the blood-pressure signal to be proportional to the provided excitation signal; as a result, the different medical devices 14 will normally expect blood-pressure signals in different voltage ranges.

In one embodiment of the invention the excitation signals from only a single blood-pressure terminal set 60a is provided directly to conductors 78 of the blood-pressure sensor 22 eliminating any conflict between differing excitation signals. A resulting pressure signal on leads 80 is then distributed back to the device-side terminals 30 of sets of blood-pressure terminal set 60a.

This blood-pressure signal on leads 80 is also received by multipliers 81a and 81b whose outputs will be sealed to provide the blood-pressure to the device-side terminals 30 of blood-pressure terminal sets 60b and 60c in the expected range. In order to obtain a desired scaling factor, the excitation signal on conductors 78 is provided to two subtracters 82a and 82b which provide difference outputs 84 indicating the amplitude of the excitation signal on conductors 78. Likewise, the excitation signals, input at blood-pressure terminal sets 60b and 60c, are received by subtracters 82c and 82d which also provide difference outputs 84 indicating the amplitude of the excitation signals provided from the connected medical devices 14. A ratio is developed by dividers 88a and 88b which, respectively, divide difference output 84 from subtractor 82a by difference output 84 from subtractor 82c, and divide the signal from subtractor 82b by the signal from subtractor 82d. The result of this division is a scaling signal 90 that indicates the amount of scaling of the blood-pressure signal on leads 80 that will be required when a blood-pressure signal is provided to the medical devices 14 connected to blood-pressure terminal sets 60b and 60c. Specifically, sealing signal 90 is provided to the respective multipliers 81a and 81b to implement the necessary scaling on the blood-pressure signal on leads 80 as it is output to the blood-pressure terminals of sets 60b and 60c.

It will be appreciated that the subtractors 82 may be implemented in the analog domain by a differencing amplifier, of the type described above for amplifier 70, as followed by a low-pass filter to provide an essentially constant difference output 84 for constant amplitude excitation. The divider 88 and multiplier 81 may be implemented by a variable gain amplifier that accepts ratiometric inputs, for example, the AD538 computational unit (ACU) available from Analog Devices of Massachusetts, USA or a similar circuit.

Figure 5:
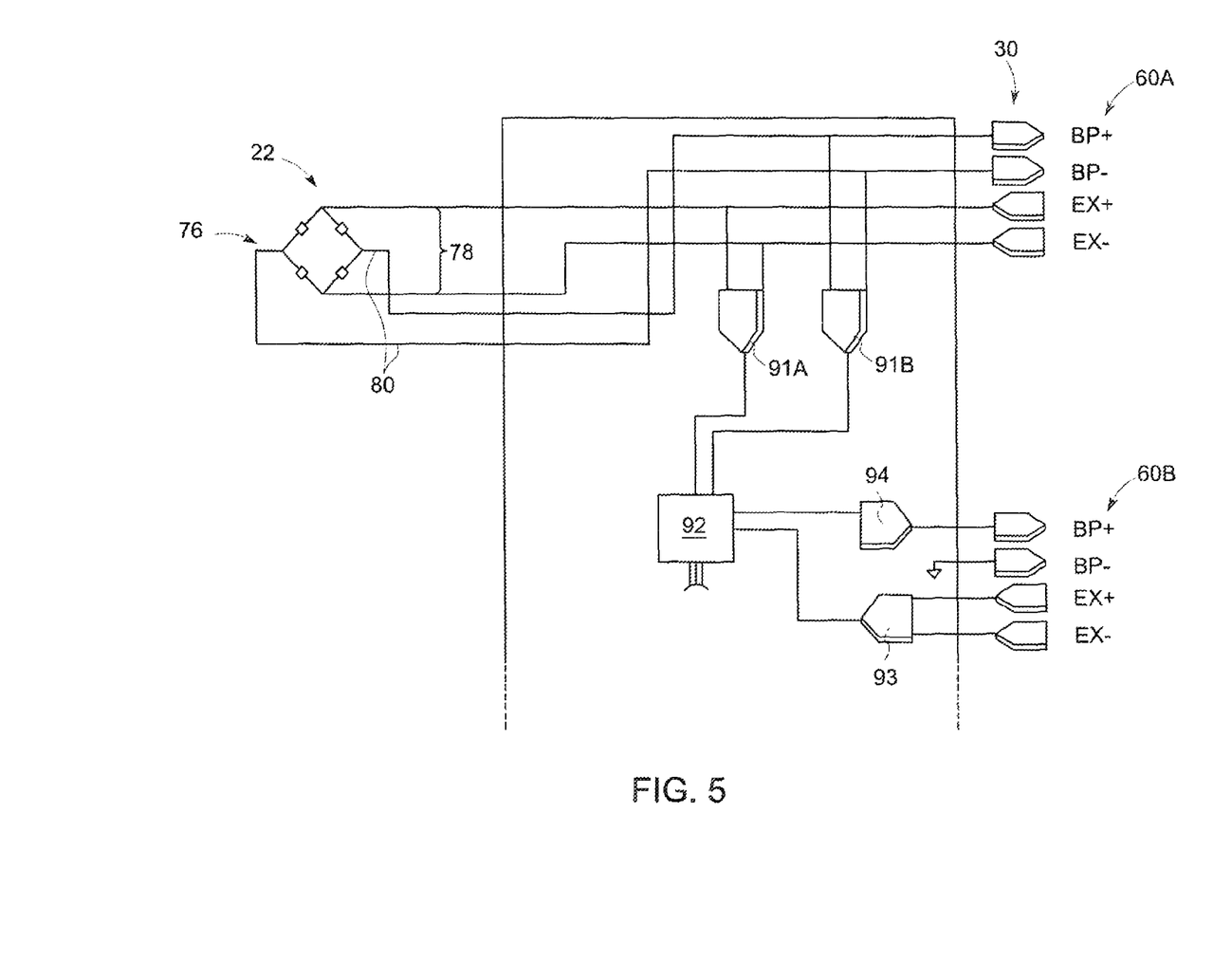
FIG. 5 is a figure similar to that of FIG. 4 showing a digital implementation of the blood-pressure subsystem.

Referring now to FIG. 5, it will be appreciated that a digital implementation of the circuit of FIG. 4 may also be created. As before, the excitation signal on conductor 78 may be taken directly from the device-side terminals 30 of blood-pressure terminal set 60a, and a blood-pressure output signal on leads 80 may be connected directly to the blood-pressure device-side terminals 30 of blood-pressure terminal set 60a.

The amplitude of the excitation signal on conductor 78 and the blood-pressure signal on leads 80 may be measured by analog-to-digital converters 91a and 91b, respectively, and provided to a microcontroller 92 as a digital signal allowing a single cycle, peak-to-peak amplitude to be extracted by a program executing on the microcontroller 92 and stored in a non-transient medium. In addition, an analog-to-digital converter 93 may receive the excitation signals from the medical devices 14 attached to terminals 30 of blood-pressure terminal sets 60b and 60c to measure the amplitude of those excitation signals. The microcontroller 92 may receive the output of these analog-to-digital converters 91 and 93 to determine peak-to-peak voltage of these excitation signals.

The microcontroller 92 may then distribute through a digital analog converter 94 associated with each of the blood-pressure terminal sets 60b and 60c a properly scaled blood-pressure signal using the mathematics implemented by the circuit of FIG. 4.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

What we claim is:

1. A multi-device connector for interfacing patient signals comprising:
   a first set of terminals receiving patient electrical conductors from patient-connected surface electrodes;
   at least a second, third and fourth set of terminals receiving device electrical conductors from medical devices requiring electrical communication with the patient electrical leads; and
   a distribution circuit comprising:
      a bidirectional electrical conductor providing a bidirectional electrical connection between the first set of terminals and only a given one of the second, third and fourth set of terminals;
a switch matrix positioned between the first set of terminals and the second, third, and fourth set of terminals operating to change the given one of the second, third, and fourth set of terminals; and
buffer amplifiers providing independent connection between each of the first set of terminals and each of the of the second, third and fourth set of terminals other than the given one of the second, third and fourth set of terminals.

2. The multi-device connector of claim 1 wherein the buffer amplifiers are high impedance unity gain amplifiers having an input impedance of over one megaohm.

3. The multi-device connector of claim 1 wherein the first, second, third, and fourth set of terminals each provide ten terminals for receiving ten patient conductors associated with a 12-lead ECG acquisition.

4. The multi-device connector of claim 3 wherein the terminals include labels indicating captions selected from the group consisting of right arm, left anal, right leg, left leg, and V1, V2, V3, V4, V5, V6 and where terminals with corresponding labels have connections by ones of the bidirectional electrical conductor and buffer amplifiers.

5. The multi-device connector of claim 1 further including at least one fifth set of electrical terminals and including differential amplifiers having inputs receiving different signals from different patient-connected surface electrodes through the first set of terminals and providing lead outputs being a difference of those inputs.

6. The multi-device connector of claim 5 wherein the lead outputs have labels providing Roman numerals.

7. The multi-device connector of claim 1 further including a visual indicator indicating which of the second, third, and fourth set of terminals is the given one of the second, third, and fourth set of terminals.

8. The multi-device connector of claim 1 further including:
a sixth set of terminals receiving patient electrical conductors from a patient-connected to an invasive blood-pressure sensor;
at least a seventh, eighth and ninth set of terminals receiving device electrical conductors from medical devices requiring electrical communication with the invasive blood-pressure sensor; wherein the invasive blood-pressure sensor receives an excitation signal to provide a blood-pressure signal and wherein each of the sixth, seventh, eighth and ninth set of terminals provide separate terminals for excitation signals and blood-pressure signals;
blood-pressure signal conductors providing a connection between the terminals for blood-pressure signals of the sixth set of terminals and the seventh set of terminals;
excitation signal conductors providing a connection between the terminals for excitation signals of the sixth set of terminals and the seventh set of terminals for communication of excitation signals between the seventh set of terminals and sixth set of terminals;
measurement circuits connected to the terminals for excitation signals of the seventh, eighth and ninth set terminals producing measurement signals measuring the excitation signals from connected medical devices; and
amplitude adjustment circuits receiving the blood-pressure signals from the sixth set of terminals and providing them independently to the eighth and ninth sets of terminals after amplitude adjustment according to a ratio of two measurement signals, the first measurement signal measuring the excitation signal from the seventh set of terminals and the second measurement signal measuring the excitation signal from a respective one of the eighth and ninth set of terminals receiving an output from a given adjustment circuit for blood-pressure signals for a respective one of the eighth and ninth set of terminals.

9. The multi-device connector of claim 8 wherein the measurement circuits are differencing amplifiers and the amplitude adjustment circuit is a variable gain amplifier accepting ratio metric inputs.

10. The multi-device connector of claim 9 wherein the differencing amplifiers are high impedance amplifiers having an input impedance of over one megaohm.

11. The multi-device connector of claim 8 wherein the measurement circuits are analog-to-digital converters and the amplitude adjustment circuit is a microprocessor communicating with separate digital analog converters for each of the eighth and ninth set of terminals.

12. The multi-device connector of claim 1 wherein each of the sixth, seventh, eighth, and ninth set of terminals includes labels indicating blood-pressure signal or excitation signal.

* * * * *

UNITED STATES PATENT AND TRADEMARK OFFICE
CERTIFICATE OF CORRECTION

PATENT NO.        : 9,591,980 B2
APPLICATION NO.   : 14/586232
DATED             : March 14, 2017
INVENTOR(S)       : Adrian F. Warner et al.

Page 1 of 1

It is certified that error appears in the above-identified patent and that said Letters Patent is hereby corrected as shown below:

In the Claims

Claim 1, Column 9, Line 9, delete "of the";

Claim 4, Column 9, Line 21, delete "anal" and substitute therefore -- arm --.

Signed and Sealed this
Sixteenth Day of May, 2017

Michelle K. Lee
*Director of the United States Patent and Trademark Office*